United States Patent [19]

Lindahl et al.

[11] Patent Number: 5,686,123

[45] Date of Patent: Nov. 11, 1997

[54] HOMOGENEOUS AND STABLE CEREAL SUSPENSION AND A METHOD OF MAKING THE SAME

[76] Inventors: Lennart Lindahl, Uardavägen 16 D., S-224 71 Lund; Inger Ahldén, Tullgatan 8 A, S-223 54 Lund; Rickard Öste, Kollegievägen 91, S-224 73 Lund; Ingegerd Sjöholm, Nöbbelövs Kyrkoväg 55, S-226 53 Lund, all of Sweden

[21] Appl. No.: 537,935

[22] PCT Filed: Sep. 14, 1994

[86] PCT No.: PCT/SE94/00857

§ 371 Date: Nov. 21, 1995

§ 102(e) Date: Nov. 21, 1995

[87] PCT Pub. No.: WO95/07628

PCT Pub. Date: Mar. 23, 1995

[30] Foreign Application Priority Data

Sep. 15, 1993 [SE] Sweden ................... 9302996

[51] Int. Cl.$^6$ ................................... A23L 1/10
[52] U.S. Cl. ............... 426/28; 426/20; 426/21; 426/31; 426/49; 426/52
[58] Field of Search ............. 426/28, 578, 658, 426/314, 21, 549, 20, 49, 52, 506, 455

[56] References Cited

U.S. PATENT DOCUMENTS 4,377,602  3/1983  Conrad ................. 426/656
4,996,063  2/1991  Inglett ................. 426/21

OTHER PUBLICATIONS

Dialog Information Services, File 51, FSTA, Dialog Assession Number 00415982, FSTA Accession Number 91–09–n0001, G.E. Inglett et al., "Maltodextrin Fat Substitute Lowers Cholesterol", Food Science & Technology, 1991, 46 (6) p.104.

*Primary Examiner*—Lien Tran
*Attorney, Agent, or Firm*—Burns, Doane, Swecker & Mathis, L.L.P.

[57] ABSTRACT

A homogeneous and stable cereal suspension having the taste and aroma of natural oats, as well as a method for the preparation thereof, is described. The cereal suspension contains intact β-glucans from the starting material and is prepared by A) dry- or wet-grinding rolled oats or otherwise heat- and water-treated oats to meal, B) suspending the oatmeal in water, if the meal has been produced by dry grinding, C) optionally centrifuging or decanting the suspension in order to remove coarse fibre particles, D) treating the suspension with β-amylase, which specifically gene-rates maltose units and has no glucanase and proteinase effect, to a viscosity of 3–0.1 Pas in the shear rate range of 10–100 $s^{-1}$, E) treating the suspension with α-amylase, which specifically gene-rates maltose units and has no glucanase and proteinase effect, to a viscosity of <0.5 Pas in the shear rate range of 10–100 $s^{-1}$, F) preferably homogenising the enzyme-treated suspension, and G) subjecting the suspension to UHT treatment (UHT= Ultra High Temperature) in order to obtain a sterile product while inactivating the enzymes added.

20 Claims, No Drawings

HOMOGENEOUS AND STABLE CEREAL SUSPENSION AND A METHOD OF MAKING THE SAME

FIELD OF THE INVENTION

This invention relates to a homogeneous and stable cereal suspension tasting and smelling like natural oats, as well as a method for the preparation thereof.

In many respects, oats is different from other cereals. Thus, it has higher protein and fat contents as well as a lower carbohydrate content than comparable cereals.

In recent years, there has been a growing interest for food made from oats. The main reason for this is that oat fibres have been found to have a wholesome effect by lowering the serum cholesterol level. Another reason is that oats contains protein of high food value as well as a considerable proportion of polyunsaturated fats. In addition, oats contains a lot of essential amino acids and minerals.

A great advantage of oats is that the whole grain can be used for making various products, once the hull has been removed. In oats, the most nutritious substances are distributed fairly evenly in the whole grain. In other cereals, the nutritious substances are frequently concentrated in some parts of the grain.

DESCRIPTION OF THE PRIOR ART

Oats is mostly used for making porridge oats and oatmeal to be added to gruel products and baby food. Oats in various forms is also added to bread, cakes, sweets, bread or cake mixes, health foods, and so forth. The functional properties of oats come in handy in such products as sauces, soups and minced meat.

U.S. Pat. No. 4,996,063 (G. F. Inglett) discloses the preparation of water-soluble dietary-fibre compositions by treating ground oat products with a-amylases. The α-amylase then serves to thin the oat starch, and any α-amylases may thus be used. The thus-produced pulverulent dietary-fibre compositions, which are colourless and lack natural aromatics, are used as additives in food. These prior-art products not only lack undesirable aromatics but are also deprived of the agreeable flavourings and aromatics found in natural oats. These products are used as fat substitutes.

SUMMARY OF THE PRESENT INVENTION

The object of the present invention is to provide a milky product based on oats.

Since it should be possible to drink the milky product as it is, the suspension has to remain stable and homogeneous for a long time and have an appealing taste and aroma. Furthermore, the product should not contain any foreign additives, such as stabilisers and artificial flavourings and aromatics.

DETAILED DESCRIPTION OF THE INVENTION AND PREFERRED EMBODIMENTS

According to the invention, this object is achieved by a homogeneous and stable cereal suspension which has the taste and aroma of natural oats and contains intact β-glucans from the starting material and which has been prepared by A) dry- or wet-grinding rolled oats or otherwise heat- and water-treated oats to meal, B) suspending the oatmeal in water, if the meal has been produced by dry grinding, C) optionally centrifuging or decanting the suspension in order to remove coarse fibre particles, D) treating the suspension with β-amylase, which specifically gene-rates maltose units and has no glucanase and proteinase effect, to a viscosity of 3–0.1 Pas in the shear rate range of 10–100 $s^{-1}$, E) treating the suspension with α-amylase, which specifically gene-rates maltose units and has no glucanase and proteinase effect, to a viscosity of <0.5 Pas in the shear rate range of 10–100 $s^{-1}$, F) preferably homogenising the enzyme-treated suspension, and G) subjecting the suspension to UHT treatment (UHT= Ultra High Temperature) in order to obtain a sterile product while inactivating the enzymes added.

The invention further comprises a method for preparing a homogeneous and stable cereal suspension that contains intact β-glucans from the starting material and has the taste and aroma of natural oats. The inventive method comprises the steps A)–G) indicated above.

The cereal suspension according to the invention can be used as an alternative to milk. Apart from the above-mentioned nutritious qualities of oats, the product should possess such properties as to be suitable for lactose-intolerant people.

The inventive product may be used as basis of or additive to ice-cream, gruel, yoghurt and milkshake, or as health drink or snack between meals.

The product is homogeneous and stable without any additives in the form of foreign stabilisers, since it contains intact β-glucans from the starting material employed.

Conveniently, the cereal suspension according to the invention is prepared on the basis of commercially-produced, pregelatinised rolled oats retaining the original taste and aroma of the oats. The rolled oats is ground to oatmeal by total, dry or wet grinding. In dry grinding, the oatmeal is suspended in water, preferably at a temperature of 50°–53° C. Also in wet grinding, use is preferably made of water having a temperature of 50°–53° C. Especially good results are obtained if the water has been deionised.

Suitably, the slurry or suspension has a weight ratio of meal to water in the range of 1:5–1:8, which corresponds to a dry solids content of 10–15%. The suspension is agitated until the meal has been dissolved and the desired extraction has been achieved. The slurry should have a pH of at least 5.

In order to remove coarse fibre particles, the suspension can then be centrifuged or decanted at 350–450 G and for about 10–15 min.

Then, β-amylase and α-amylase are added. The β-amylase should be a β-amylase that specifically generates maltose units and has no glucanase and proteinase effect, preferably 1,4-α-D-glucan maltohydrolase. The α-amylase should be an α-amylase which specifically generates maltose units and has no glucanase and proteinase effect.

The amount of enzyme, the temperature of the slurry, the agitation time and the pH value are optimised after the gelatinisation of starch in order to obtain a product of suitable viscosity after heating. The choice of suitable parameters is influenced by several factors, such as the starting material employed, the enzymes added, and the desired viscosity of the end product.

The treatment with β-amylase is carried out such that the suspension obtains a viscosity of 3–0.1 Pas in the shear rate range of 10–100 $s^{-1}$. The treatment with α-amylase is carried out such that the suspension obtains a viscosity of <0.5 Pas in the same shear rate range.

The product is then homogenised, suitably at a temperature of 72°–75° C. and a pressure of 200–250 bar.

Finally, the product is subjected to UHT treatment (Food Engineering and Dairy Technology, H. G. Kessler, Verlag A. Kessler, 1981, Chapter 6, pp 139–207) in view of sterilising it while inactivating the enzymes added. Conveniently, the end product is packed aseptically.

The maximum dry solids content of the product is in the range of 10–15%. The viscosity at room temperature is below 0.5 Pas. The β-glucan values (based on the dry solids content) were determined with the aid of a so-called Biocon kit from Biocon Pry. Ltd., Australia, as follows:

Cereal product not subjected to enzyme treatment: 6.5% on DS

Cereal product+β-amylase: 5.8% on DS

The invention will now be described in more detail with the aid of two Examples.

EXAMPLE 1

No Centrifugation

Immediately before the other steps of the inventive method, steam-processed rolled oats is ground to meal (100% grinding). It is an advantage if the meal is finely ground such that it can pass through a bolter with a mesh of 0.8–1 mm. 1 kg of meal is mixed with 6 l of water while agitated. The water should have a temperature of 50°–53° C.

In a first enzyme-treatment step, β-amylase is added to the formed slurry under continuous agitation. In enzyme step 1, the incubation temperature is 53°–55° C. Enzyme step 1 proceeds until the viscosity of the slurry has fallen to a value of 3–0.1 Pas in the shear rate range of 10–100 $s^{-1}$.

Then, α-amylase which specifically generates maltose units is added to the slurry in a second enzyme-treatment step. In enzyme step 2, the incubation temperature is 55°–57° C. The incubation with α-amylase proceeds until the slurry has obtained a viscosity of <0.5 Pas in the shear rate range indicated above.

Then, the slurry is homogenised at a pressure of 200 bar (homogenisation should be carried out in the range of 160–250 bar) and at a temperature of 72°–75° C. The slurry is then immediately treated by indirect vapour at a temperature of 137°–138° C. and for 3–4 s in order to sterilise the product (killing bacteria and spore-forming agents) before it is packed aseptically. At the same time, the enzymes added are totally inactivated.

The resulting oat base has the following composition

| | |
|---|---|
| % DS | 13.4 |
| % protein on DS | 2.2 |
| % fat on DS | 0.8 |
| % fibres, total on DS | 0.8 |
| of which % soluble fibres | 0.34 |
| % insoluble fibres | 0.46 |
| % starch on DS (incl. * sugars) | 7.9 |
| * sugars, mg/g DS: | |
| Fructose | — |
| Glucose | 2.2 |
| Saccharose | 11.8 |
| Maltose | 316.0 |
| Raffinose | 3.0 |
| Maltotriose | 7.8 |

EXAMPLE 2

With Centrifugation

Example 1 was repeated, but with a separation step for removing coarse fibre particles. The separation was produced by centrifugation at 400 G before the first enzyme incubation.

We claim:

1. A homogeneous and stable cereal suspension having the taste and aroma of natural oats, which contains intact β-glucans prepared by the following steps
   A) dry- or wet-grinding rolled oats or otherwise heat- and water-treated oats to meal,
   B) suspending the oatmeal in water to form a suspension if the meal has been produced by dry grinding,
   C) optionally centrifuging or decanting the suspension in order to remove coarse fibre particles,
   D) treating the suspension with β-amylase in a first enzyme treatment step which specifically gene-rates maltose units and has no glucanase and proteinase activity, to a viscosity of 3–0.1 Pas in the shear rate range of 10–100 $s^{-1}$,
   E) treating the suspension with α-amylase in a second enzyme treatment step which spiecifically gene-rates maltose units and has no glucanase and proteinase activity, to a viscosity of <0.5 Pas in the shear rate range of 10–100 $s^{-1}$,
   F) optionally homogenising the enzyme-treated suspension, and
   G) subjecting the suspension which has been treated with B-amylase and alpha amylase to UHT treatment (UHT=Ultra High Temperature) in order to obtain a sterile product and to inactivate the enzymes added.

2. A method for preparing a homogeneous and stable cereal suspension containing intact β-glucans and having the taste and aroma of natural oats, comprising the steps of
   A) dry- or wet-grinding rolled oats or otherwise heat- and water-treated oats to meal,
   B) suspending the oatmeal in water to form a suspension if the meal has been produced by dry grinding,
   C) optionally centrifuging or decanting the suspension in order to remove coarse fibre particles,
   D) treating the suspension with β-amylase in a first enzyme treatment step which specifically gene-rates maltose units and has no glucanase and proteinase activity, to a viscosity of 3–0.1 Pas in the shear rate range of 10–100 $s^{-1}$,
   E) treating the suspension with α-amylase in a second enzyme treatment step, which specifically gene-rates maltose units and has no glucanase and proteinase activity, to a viscosity of <0.5 Pas in the shear rate range of 10–100 $s^{-1}$,
   F) optionally homogenising the enzyme-treated suspension, and
   G) subjecting the suspension which has been treated with β-amylase and alpha amylase to UHT treatment (UHT= Ultra High Temperature) in order to obtain a sterile product and to inactivate the enzymes added.

3. A method as set forth in claim 2, wherein deionised water is used in the wet grinding of step A) and the suspension of step B).

4. A method as set forth in claim 2, comprising suspending the oatmeal to a dry solids content of 10–15% in step B).

5. A method as set forth in claim 2, comprising using water having a temperature of 50°–53° C. in the wet grinding of step A) and the suspension of step B).

6. A method as set forth in claim 2, comprising using 1,4-α-D-glucan maltohydrolase as β-amylase in step D).

7. A method as set forth in claim 2, comprising packing the homogeneous and stable cereal product aseptically.

8. A method as set forth in claim 3, comprising suspending the oatmeal to a dry solids content of 10–15 % in step B).

9. A method as set forth in claim 3, comprising using water having a temperature of 50°–53° C. in the wet grinding of step A) and the suspension of step B).

10. A method as set forth in claim 4, comprising using water of temperature of 50°–53° C. in the wet grinding of step A) and the suspension of step B).

11. A method as set forth in claim 3, comprising using 1,4-α-D-glucan maltohydrolase as β-amylase in step D).

12. A method as set forth in claim 4, comprising using 1,4-α-D-glucan maltohydrolase as β-amylase in step D).

13. A method as set forth in claim 5, comprising using 1,4-α-D-glucan maltohydrolase as B-amylase in step D).

14. A method as set forth in claim 3, comprising packing the homogenous and stable cereal product aseptically.

15. A method as set forth in claim 4, comprising packing the homogenous and stable cereal product aseptically.

16. A method as set forth in claim 5, comprising packing the homogenous and stable cereal product aseptically.

17. A method as set forth in claim 6, comprising packing the homogenous and stable cereal product aseptically.

18. A method as set forth in claim 8, comprising using water having a temperature of 50°–53° C. in the wet grinding of step A) and the suspension of step B).

19. A method as set forth in claim 8, comprising using 1,4-α-D-glucan maltohydrolase as β-amylase in step D).

20. A method as set forth in claim 8, comprising packing the homogenous and stable cereal product aseptically.

* * * * *